US012721545B2

(12) United States Patent
Burwinkel et al.

(10) Patent No.: US 12,721,545 B2
(45) Date of Patent: Sep. 1, 2026

(54) ALERTNESS DETERMINATION FOR NON-ALERT DETECTION USING EAR-WORN ELECTRONIC DEVICES

(71) Applicant: Starkey Laboratories, Inc., Eden Prairie, MN (US)

(72) Inventors: Justin R. Burwinkel, Eden Prairie, MN (US); Kyle Olson, St. Louis Park, MN (US); Jeffrey Paul Solum, Greenwood, MN (US); Yoshi Kasahara, Chaska, MN (US); Gregory J. Haubrich, Champlin, MN (US); Christine Tan, Eden Prairie, MN (US)

(73) Assignee: Starkey Laboratories, Inc., Eden Prairie, MN (US)

( * ) Notice: Subject to any disclaimer, the term of this patent is extended or adjusted under 35 U.S.C. 154(b) by 0 days.

(21) Appl. No.: 18/731,613

(22) Filed: Jun. 3, 2024

(65) Prior Publication Data

US 2024/0315598 A1 Sep. 26, 2024

Related U.S. Application Data

(62) Division of application No. 17/206,342, filed on Mar. 19, 2021, now Pat. No. 12,023,147.

(Continued)

(51) Int. Cl.

*A61B 5/11* (2006.01)
*A61B 5/00* (2006.01)

(Continued)

(52) U.S. Cl.

CPC .................. *A61B 5/11* (2013.01); *A61B 5/01* (2013.01); *A61B 5/0816* (2013.01); *A61B 5/162* (2013.01); *A61B 5/163* (2017.08); *A61B 5/165* (2013.01); *A61B 5/18* (2013.01); *A61B 5/398* (2021.01); *A61B 5/4845* (2013.01); *A61B 5/6817* (2013.01); *A61B 5/7405* (2013.01); *A61B 5/742* (2013.01); *A61B 5/7455* (2013.01);

(Continued)

(58) Field of Classification Search

CPC .. A61B 5/11; A61B 5/163; A61B 5/01; A61B 5/0816; A61B 5/162; A61B 5/165; A61B 5/18; A61B 5/4845; A61B 5/6817; A61B 5/7405; A61B 5/742; A61B 5/7455; A61B 2503/22; A61B 2503/40; G16H 20/30; G16H 40/67; B60W 60/0051; B60W 40/08

USPC .......................................................... 340/576

See application file for complete search history.

(56) References Cited

U.S. PATENT DOCUMENTS

| | | | |
|---|---|---|---|
| 6,920,229 | B2 | 7/2005 | Boesen |
| 7,532,964 | B2 | 5/2009 | Fujita et al. |

(Continued)

FOREIGN PATENT DOCUMENTS

| | | |
|---|---|---|
| EP | 2071875 | 7/2009 |
| JP | 4980988 | 4/2012 |
| KR | 20-2017-0004127 | 12/2017 |

*Primary Examiner* — Zhen Y Wu

(74) *Attorney, Agent, or Firm* — Mueting Raasch Group

(57) ABSTRACT

Techniques to detect a non-alert state of a user may include receiving sensor data from an ear-worn electronic device disposed at least partially in the ear of a user, determining an alertness state of the user based on the sensor data, and providing alert data in response to the alertness state comprising a non-alert state to a user stimulation interface of the ear-worn electronic device or to an external device.

22 Claims, 5 Drawing Sheets

Related U.S. Application Data

(60) Provisional application No. 62/992,325, filed on Mar. 20, 2020.

(51) Int. Cl.

*A61B 5/01* (2006.01)
*A61B 5/08* (2006.01)
*A61B 5/16* (2006.01)
*A61B 5/18* (2006.01)
*A61B 5/398* (2021.01)
*B60W 40/08* (2012.01)
*B60W 60/00* (2020.01)
*G16H 20/30* (2018.01)
*G16H 40/67* (2018.01)

(52) U.S. Cl.

CPC ........ *B60W 40/08* (2013.01); *B60W 60/0051* (2020.02); *G16H 20/30* (2018.01); *G16H 40/67* (2018.01); *A61B 2503/22* (2013.01); *A61B 2503/40* (2013.01)

(56) References Cited

U.S. PATENT DOCUMENTS 7,650,004 B2 1/2010 Durant
8,022,831 B1 9/2011 Wood-Eyre
8,355,794 B2 1/2013 Lineaweaver et al.
8,487,775 B2 7/2013 Victor et al.
8,652,040 B2 * 2/2014 LeBoeuf ............... A61B 5/1118 600/301
9,007,220 B2 * 4/2015 Johns ..................... G08B 21/06 340/576
9,142,130 B1 * 9/2015 Dukish .................. G08G 1/095
9,260,013 B2 2/2016 Kume et al.
9,579,060 B1 * 2/2017 Lisy ..................... A61B 5/6803
9,763,614 B2 * 9/2017 Geller ...................... A61B 5/11
9,838,771 B1 * 12/2017 Masaki ................ G01R 33/072
10,045,130 B2 * 8/2018 Masaki ................. G01P 15/003
10,081,317 B2 9/2018 Naboulsi
10,342,482 B1 * 7/2019 Lisy ..................... A61B 5/6803
10,799,122 B2 * 10/2020 Tzvieli ................. A61B 5/6803
10,874,346 B1 * 12/2020 Lisy ..................... A61B 5/6803
10,898,133 B1 * 1/2021 Lisy ..................... A61B 5/6803
11,170,240 B2 * 11/2021 Ardelean ............. G06V 20/597
11,298,064 B1 * 4/2022 Lisy ..................... A61B 5/6803
11,338,106 B2 * 5/2022 Fabry ................... A61B 5/1122
2001/0028309 A1 * 10/2001 Torch .................. A61B 5/1103 340/576
2006/0011144 A1 * 1/2006 Kates ..................... G01S 15/86 119/859
2006/0214807 A1 * 9/2006 Tengshe ................. G08B 21/06 340/576
2010/0280338 A1 * 11/2010 Chou ..................... A61B 5/486 600/301
2012/0197093 A1 * 8/2012 LeBoeuf .............. A61B 5/7203 250/226
2012/0293773 A1 * 11/2012 Publicover ........... A61B 3/0008 351/210
2014/0058220 A1 * 2/2014 LeBoeuf .............. A61B 5/6887 600/407
2015/0363657 A1 * 12/2015 Shigemura ............... A61B 5/18 382/104
2016/0014497 A1 * 1/2016 Chizi .................. H04R 1/1091 381/74
2016/0119726 A1 4/2016 Pontoppidan
2017/0265798 A1 * 9/2017 Sales ...................... G06V 20/35
2017/0313190 A1 * 11/2017 Shimada ................ G08B 21/06
2017/0347177 A1 * 11/2017 Masaki .............. A61B 5/02055
2017/0347178 A1 * 11/2017 Masaki ................ H04R 1/1091
2017/0347179 A1 * 11/2017 Masaki ................ H04R 1/1016
2018/0009442 A1 * 1/2018 Spasojevic ........... A61B 5/4064
2018/0242859 A1 * 8/2018 LeBoeuf .............. A61B 5/6817
2018/0268695 A1 * 9/2018 Agnew ................. B60W 50/14
2019/0121356 A1 * 4/2019 Migneco .............. A61B 5/0077
2019/0366844 A1 * 12/2019 Yoon ..................... B60W 50/14
2020/0085312 A1 * 3/2020 Tzvieli ............... A61B 5/02055
2020/0112755 A1 * 4/2020 Seshadri .............. G06N 3/0455
2020/0218914 A1 * 7/2020 Ardelean ........... B60H 1/00742
2021/0290135 A1 * 9/2021 Burwinkel ........... H04R 1/1041
2024/0315598 A1 * 9/2024 Burwinkel ............... A61B 5/11

* cited by examiner

ALERTNESS DETERMINATION FOR NON-ALERT DETECTION USING EAR-WORN ELECTRONIC DEVICES

This application is a divisional of U.S. patent application Ser. No. 17/206,342, filed Mar. 19, 2021, which claims the benefit of U.S. Provisional Application No. 62/992,325, filed Mar. 20, 2020, the disclosures of which are incorporated by reference herein in their entireties.

The present technology is generally related to ear-worn electronic devices and, in particular, to ear-worn electronic devices configured to detect a non-alert state of a user.

Hearing devices provide sound for the wearer. Some examples of hearing devices are headsets, hearing aids, speakers, cochlear implants, bone conduction devices, and personal listening devices. For example, hearing aids provide amplification to compensate for hearing loss by transmitting amplified sounds to a wearer's ear canals. Hearing devices may include various types of sensors and may be operably coupled to other devices to facilitate various functionality.

SUMMARY

The techniques of this disclosure generally relate to techniques to detect a non-alert state of a user of a machine, such as a vehicle, aircraft, boats, trains, forklifts, agricultural machinery, or industrial equipment, or even stationary heavy machinery, using ear-worn electronic devices or related systems. Ear-worn electronic devices, such as hearing aids, may be used to detect the non-alert state of the user. Alerts may be generated when the user is in a non-alert state. Detection of alertness states of the user may be limited to a particular alertness mode, which may reduce false positive or otherwise unnecessary alerts. In some cases, when a determined alertness state of the user crosses a threshold, the ear-worn electronic device or system may initiate corrective actions, including audible alerts or activation of operably connected devices.

In independent aspect A1, a method includes: receiving sensor data from an ear-worn electronic device disposed at least partially in the ear of a user; determining an alertness state of the user based on the sensor data; and providing alert data in response to the alertness state including a non-alert state to a user stimulation interface of the ear-worn electronic device or to an external device.

In aspect A2, aspect A1 further includes wherein the sensor data includes one or more of the following: motion data indicating a head position of the user; and motion data indicating head movements of the user.

In aspect A3, aspect A1 or A2 further includes wherein the sensor data includes sound data from at least one microphone of the ear-worn electronic device indicating one or more of the following: non-alert types of sounds; and a reaction speed below a threshold.

In aspect A4, any preceding A aspect further includes wherein the sensor data includes physiological data including one or more of the following: data indicating a respiration rate of the user; data indicating surprise of the user; data indicating a temperature of the user; data indicating physiological electrical signals of the user indicative of eye gaze; and data indicating head motion or position of the user.

In aspect A5, any preceding A aspect further includes wherein the sensor data includes one or more of the following: data indicating a reaction speed of the user; and emotional state data.

In aspect A6, any preceding A aspect further includes determining the alertness state of the user further based on external sensor data.

In aspect A7, aspect A6 further includes wherein the external sensor data includes motion data from at least one motion sensor indicating arm movements of the user.

In aspect A8, aspect A6 or A7 further includes wherein the external sensor data includes visual data from at least one optical sensor including eye gaze data of the user.

In aspect A9, aspect A8 further includes wherein the external sensor data includes driving data, the method further including determining a user operation adherence level based on the driving data.

In aspect A10, any aspect A6 to A9 further includes wherein the external sensor data includes chemical sensor data indicating an impairment level.

In aspect A11, any preceding A aspect further includes receiving support animal data indicating a reaction of a support animal of the user.

In aspect A12, any preceding A aspect further includes: determining a driver error score based on a current driver score to a predetermined baseline driver score; and determining an alertness state of the user further based on the driver error score.

In aspect A13, any preceding A aspect further includes updating a model to determine the alertness state of the user based on historical user data to reduce false positive indications of non-alert states.

In aspect A14, any preceding A aspect further includes providing the alert data to an external device to activate an autonomous or semi-autonomous operational mode of a machine being operated by the user.

In aspect A15, any preceding A aspect further includes wherein a user-perceptible alert is provided in response to the alert data including one of more of the following: an audible alert, a haptic alert, an electrical stimulation alert, and a visual alert.

In independent aspect B1, an ear-worn electronic device configured to be worn by a user includes: a housing configured to be disposed at least partially in the ear of the user when worn by the user; a user stimulation interface disposed in or on the housing and configured to provide stimulation to the user based on stimulation data; a microphone disposed in or on the housing and configured to provide sound data based on monitored ambient sound; one or more additional sensors including a motion sensor, a magnetic sensor, or both to provide additional sensor data, the motion sensor disposable in the housing and configured to provide motion data based on movement of the ear of the user, the magnetic sensor disposable in the housing and configured to provide magnetic data; and a controller disposed in the housing, the controller being operably coupled to the user stimulation interface to provide stimulation data, the microphone to receive sound data, and the one or more additional sensors to receive the additional sensor data. The controller is configured to: receive sensor data including the sound data, the additional sensor data, or both; and determine an alertness state of the user based on the sensor data.

In aspect B2, aspect B1 further includes wherein the controller is further configured to provide alert data in response to the alertness state including a non-alert state to one or more of the following: the user stimulation interface and a communication interface of the controller.

In independent aspect C1, a system includes an ear-worn electronic device configured to be worn by a user. The device includes a housing configured to be disposed at least partially in the ear of the user when worn by the user; a user stimulation interface disposed in or on the housing and configured to provide stimulation to the user based on stimulation data; a microphone disposed in or on the housing and configured to provide sound data based on monitored ambient sound; and one or more additional sensors including a motion sensor, a magnetic sensor, or both to provide additional sensor data, the motion sensor disposable in the housing and configured to provide motion data based on movement of the ear of the user, the magnetic sensor disposable in the housing and configured to provide magnetic data. The system also includes a controller operably coupled to the ear-worn electronic device to provide the stimulation data, receive the sound data, and receive the additional sensor data. The controller is configured to: receive sensor data from the ear-worn electronic device including the sound data, the additional sensor data, or both; and determine an alertness state of the user based on the sensor data.

In aspect C2, aspect C1 further includes wherein the controller is further configured to provide alert data in response to the alertness state including a non-alert state to one or more of the following: the user stimulation interface and a communication interface of the controller.

In aspect C3, aspect C1 or C2 further includes an external device, the external device including at least one of the following: a handheld user device, a separate user-worn device, a machine computing device, and a remote electronic device.

In aspect D1, a device according to any B aspect or a system according to any C aspect further includes wherein the controller is further configured to carry out any one of the methods according to any A aspect.

BRIEF DESCRIPTION OF THE DRAWINGS

Throughout the specification reference is made to the appended drawings wherein.

The figures are not necessarily to scale. Like numbers used in the figures refer to like components. However, it will be understood that the use of a number to refer to a component in a given figure is not intended to limit the component in another figure labeled with the same number.

DETAILED DESCRIPTION

Figure 1:
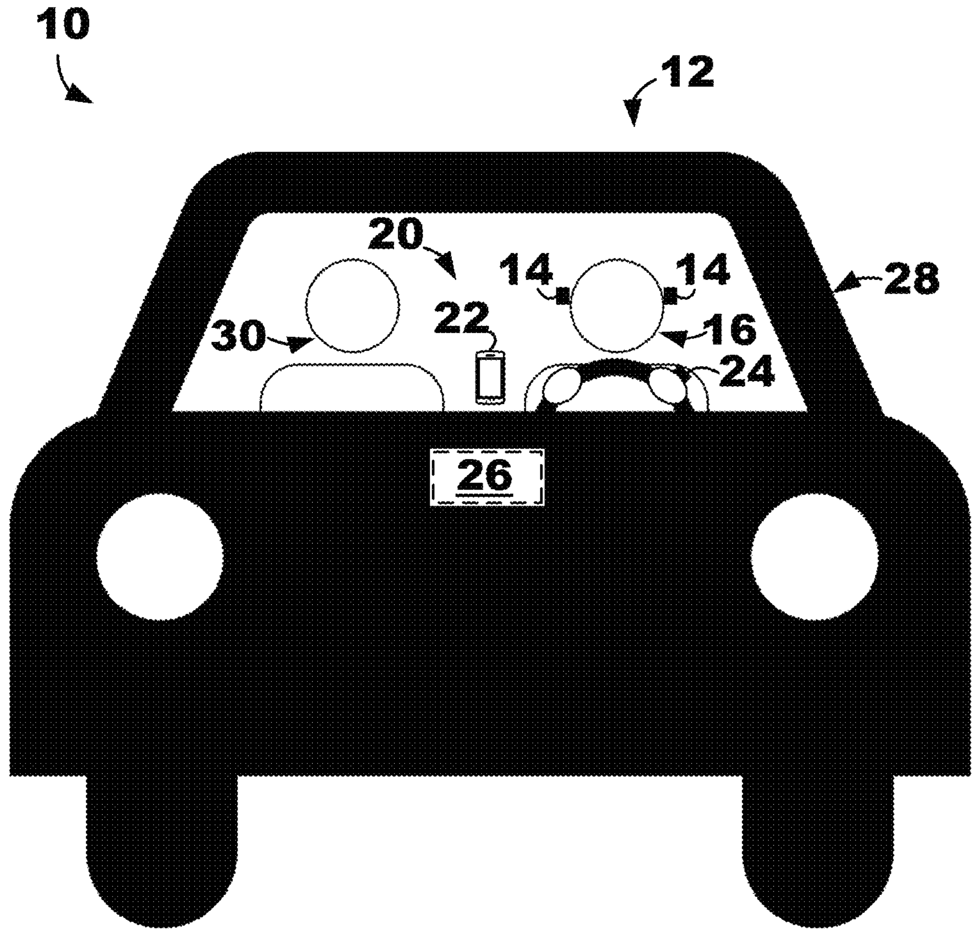
FIG. 1 is a schematic diagram showing one example of an environment for use with a non-alert detection system including one or more ear-worn electronic devices to facilitate detection of one or more non-alert states of a user.

The present disclosure relates techniques to detect a non-alert state of a user of a machine, such as a vehicle, aircraft, boats, trains, forklifts, agricultural machinery, or industrial equipment, or even stationary heavy machinery, using ear-worn electronic devices or related systems. Ear-worn electronic devices, such as hearing aids, equipped with wireless communication radios and various sensors, such as multi-axis inertial measurement units (IMUs) may be used to facilitate improved user experiences, for example, by allowing streaming audio, programming, and data collection in conjunction with other devices, as well as to detect the non-alert state of the user. Alerts may be generated when the user is in a non-alert state, such as drowsiness, sleepiness, seizing, fainting, stroke, or other impairing or incapacitating condition. Detection of alertness states of the user may be limited to a particular alertness mode, which may reduce false positive or otherwise unnecessary alerts. In some cases, when a determined alertness state of the user crosses a threshold, which may be adapted over time or on a per user basis, then the ear-worn electronic device or system may initiate corrective actions, including audible alerts or activation of operably connected devices.

In some embodiments, techniques may include detecting when the user (a driver or operator) of a motor vehicle or other machine has become drowsy or otherwise impaired and warn the driver through alerts that the driver is dozing off or becoming incapacitated for the purpose of operating the motor vehicle. Suitable alerts may include sound, haptic, visual, or electrical stimulus. Techniques may include detecting when the user of power tools or other heavy equipment is becoming drowsy or otherwise impaired and warn the operator through sound alerts that the operator is dozing off or becoming incapacitated for the purpose of operating the power equipment. Further, techniques may include detecting when the user is becoming drowsy and place the vehicle or equipment into autonomous mode of operation when the equipment can safely shut down or cease operation.

In some embodiments, indicative factors contributing to an additive effect leading to fatigue may be used to determine whether to initiate the alertness mode or to determine the alertness level. Such factors may include user historical data, such as a user's circadian rhythm, wake time, and physical activity level. Other indicative factors may include emotional state, social engagements (such as conversations), and active listening (such as reaction speed), which may be monitored using emotion monitoring, social engagement monitoring, and active listening detection, respectively.

A system for ear-worn electronic devices, such as hearing instruments or ear buds, may incorporate ear-worn electronic components for signal processing, sensing multi-axis motion (such as an IMU), a user stimulation interface for outputting stimulation signals (such as audio or sound), and optionally a wireless radio. The system may determine when the user of a motor vehicle or other machine is drowsy or otherwise non-alert based on head motion or position. In some embodiments, the system may alert the operator using an audible alert. The audible alert may be played to the user through the receiver worn by the user or through the vehicle entertainment system. In other embodiments, the system may alert the machine computing system of the motor vehicle or other machine, which may be configured to provide driver assistance or an autonomous control mode, that the user may be drowsy or otherwise non-alert such that the machine computing system can take automatic corrective action to avoid other vehicles or obstacles during operation. The system may determine the user is drowsy or otherwise non-alert based on various data, such as IMU data (motion data), audio information (sound data), GPS information, or any combination thereof.

Many examples in the following description relate to motor vehicle driving by the user. The techniques described herein may be particularly beneficial to truck drivers who may have hearing loss and use car-worn electronic devices (such as hearing aids) as occupational mandates for hearing loss correction. However, the techniques described herein may be applicable to any situation in which a user wishes to remain alert or is at risk of being non-alert, whether or not the user is operating machinery. For example, the user may be simply performing desk work. Machines other than cars or trucks that may be used with the system, for example, include aircraft, boats, trains, forklifts, agricultural machinery, or industrial equipment.

It is understood that the embodiments described herein may be used with any car-worn or ear-level electronic device without departing from the scope of this disclosure. The devices depicted in the figures are intended to demonstrate the subject matter, but not in a limited, exhaustive, or exclusive sense. Ear-worn electronic hearing devices (referred to herein as "hearing devices") typically include an enclosure, such as a housing or shell, within or on which internal components are disposed. Typical components of a hearing device can include a processor (such as a digital signal processor or DSP), memory circuitry, power management circuitry, one or more communication devices (such as a radio, a near-field magnetic induction (NFMI) device), one or more antennas, one or more microphones, one or more telecoils, and a receiver/speaker, for example. Hearing devices can incorporate a long-range communication device, such as a Bluetooth® transceiver or other type of radio frequency (RF) transceiver. A communication device (such as a radio or NFMI device) of a hearing device can be configured to facilitate communication between a left ear device and a right ear device of the hearing device. Hearing devices can also incorporate a motion sensor or sensors that can be used to switch input between left and right hearing devices (for example, assuming left and right devices have varying orientation of the motion sensor(s), such as a telecoil) so that optimal audio can be sent to the opposite hearing device.

Ear-worn electronic devices of the present disclosure can incorporate an antenna operatively coupled to a high-frequency transceiver, such as a 2.4 GHz radio. The RF transceiver can conform to an IEEE 802.11 (e.g., WiFi®) or Bluetooth® (such as BLE, Bluetooth® 4. 2, 5.0, 5.1 or later) specification, for example. It is understood that hearing devices of the present disclosure can employ other transceivers or radios, such as a 900 MHz radio. Hearing devices of the present disclosure can be configured to receive streaming audio (such as digital audio data or files) from an electronic or digital source. Representative electronic/digital sources (such as accessory devices) include an assistive listening system, a machine computing system (such as a car audio system), a TV streamer, a TV, a radio, a smartphone, a laptop, a cell phone/entertainment device (CPED), a consumer electronic device, or other electronic device that serves as a source of digital audio data or other types of data files. Hearing devices of the present disclosure can be configured to effect bi-directional communication (such as wireless communication) of data with an external source, such as a remote server via the Internet or other communication infrastructure. Hearing devices that include a left ear device and a right ear device can be configured to effect bi-directional communication (such as wireless communication) therebetween, so as to implement ear-to-ear communication between the left and right ear devices.

As used herein, the term "hearing device" of the present disclosure refers to a wide variety of ear-level electronic devices that can aid a person with impaired hearing. The term hearing device also refers to a wide variety of devices that can produce processed sound for persons with normal hearing. Hearing devices of the present disclosure include hearables (e.g., wearable earphones, headphones, earbuds, audio monitors, virtual reality headsets), hearing aids (e.g., hearing instruments), cochlear implants, and bone-conduction devices, for example. Hearing devices include, but are not limited to, behind-the-ear (BTE), in-the-ear (ITE), in-the-canal (ITC), invisible-in-canal (IIC), receiver-in-canal (RIC), receiver-in-the-ear (RITE) or completely-in-the-canal (CIC) type hearing devices or some combination of the above. Throughout this disclosure, reference is made to a "hearing device," which is understood to refer to a system including a single left ear device, a single right ear device, or a combination of a left ear device and a right ear device.

As used herein, the term "non-alert" refers to a state of the user in which reaction speeds to stimulus may be below a particular threshold, slowed, or impaired. Non-limiting examples of non-alert states include a user being fatigued, drowsy, or impaired. The non-alert state may be natural, for example, due to the time of day and the user's sleep cycle (such as nighttime) or may be due to other influences (such as alcohol or medication).

The term "or" is generally employed in its inclusive sense, for example, to mean "and/or" unless the context clearly dictates otherwise. The term "and/or" means one or all of the listed elements or a combination of at least two of the listed elements.

The terms "coupled" or "connected" refer to elements being attached to each other either directly (in direct contact with each other) or indirectly (having one or more elements between and attaching the two elements). Either term may be replaced to "couplable" or "connectable" to describe that the elements are configured to be coupled or connected. In addition, either term may be modified by "operatively" and "operably," which may be used interchangeably, to describe that the coupling or connection is configured to allow the components to interact to carry out functionality (for example, a radio chip may be operably operatively coupled to an antenna element to provide a radio frequency electromagnetic signal for wireless communication).

FIG. 1 is a schematic diagram showing one example of an environment 10 for use with a non-alert detection system 12 including one or more ear-worn electronic devices 14 to facilitate detection of one or more non-alert states of a user 16 (or a wearer). In the illustrated embodiment, the system 12 includes two ear-worn electronic devices 14. The system 12 may include a left, or left-sided, device and a right, or right-sided device. Each of the devices 14 is configured to be worn by the user 16.

In general, the device 14 is configured for use in, on, or about an ear of the user 16. In some embodiments, the device 14 may be used as a single hearing device configured for monaural or single-ear operation or one of a pair of hearing devices configured for binaural or dual-ear operation, as illustrated. Each of the devices 14 includes a housing, which may be configured to be disposed at least partially in one of the ears of the user 16 when the respective device is worn by the user. Various components may be situated, supported, or otherwise disposed in the housing 32 (FIG. 4) of the device 14. Various components of the device 14 may include one or more sensors (see FIGS. 3 and 4), which may provide sensor data for use by the device or other devices operably coupled to the device.

The system 12 may include a controller 18 (see FIGS. 3 and 4), which may be operably coupled to the one or more ear-worn electronic devices 14, for example, to receive the sensor data from the one or more sensors. Any suitable type of controller 18 may be used.

The system 12 may include one or more external devices 20, which may be operably coupled to the one or more ear-worn electronic devices 14 or the controller 18. Various components of the system 12 may be operably coupled in any suitable manner, such as by wired or wireless connection.

Any suitable type of external device 20 may be used. Non-limiting examples of external devices 20 include one or more of the following: a handheld user device 22 (such as a smartphone, tablet, or laptop), a separate user-worn device 24 (such as a smartwatch worn on the wrist, hand, or arm of the user 16 or other non-ear-worn device), a machine computing device 26 (such as a navigation computer of a vehicle or heavy machinery), and a remote electronic device 38 (such as a data server or cloud-based system connected over the internet 36 to store or process data). In general, sensors at least partially or entirely disposed in one or more external devices 20 may be described as external sensors, which may provide external sensor data.

The system 12 may be used in any suitable environment. In some embodiments, the system 12 may be used with a machine 28 and the user 16 may be the operator of the machine. In the illustrated embodiment, the system 12 is used in a vehicle as the machine 28. In addition to the user 16, the machine 28 may also carry a passenger 30. In some embodiments, the system 12 may be used to determine whether the user 16 is the operator or the passenger as described herein in more detail.

Various aspects of the system 12 may be used to reduce false activations of the non-alert states or "false positives." In general, the system 12 may use a calibrated determination of whether to initiate an alertness mode and a calibrated determination of whether the user 16 is non-alert to more accurately predict whether the user is non-alert based on various sensor data.

In some embodiments, the controller 18 of the system 12 may be configured to receive sensor data from one or more of the devices 14. The sensor data may include one or more of the following: the sound data, the motion data, and the magnetic data. Additionally, or alternatively, other types of sensor data may also be included. The controller 18 of the system 12 may also be configured to automatically determine whether to initiate an alertness mode of the controller based on the sensor data. Also, the controller 18 of the system 12 may be configured to determine an alertness state of the user in response to determining to initiate the alertness mode.

In some additional embodiments, the controller 18 of the system may be configured to receive sensor data from one or more of the devices 14. The senor data may include one or more of the following: the sound data, the motion data, and the magnetic data. The controller 18 of the system 12 may also be configured to determine an alertness state of the user based on the sensor data. Also, the controller 18 of the system may be configured to provide alert data in response to the alertness state including a non-alert state. For example, the alert data may be provided to one or more of the following: a user stimulation interface of one or more of the devices 14 or to one or more of the external devices 20. In some embodiments, the alert data may be provided to the one or more external devices 20 using a data communication interface 66 (see FIGS. 3 and 4) of the controller 18.

Figure 2:
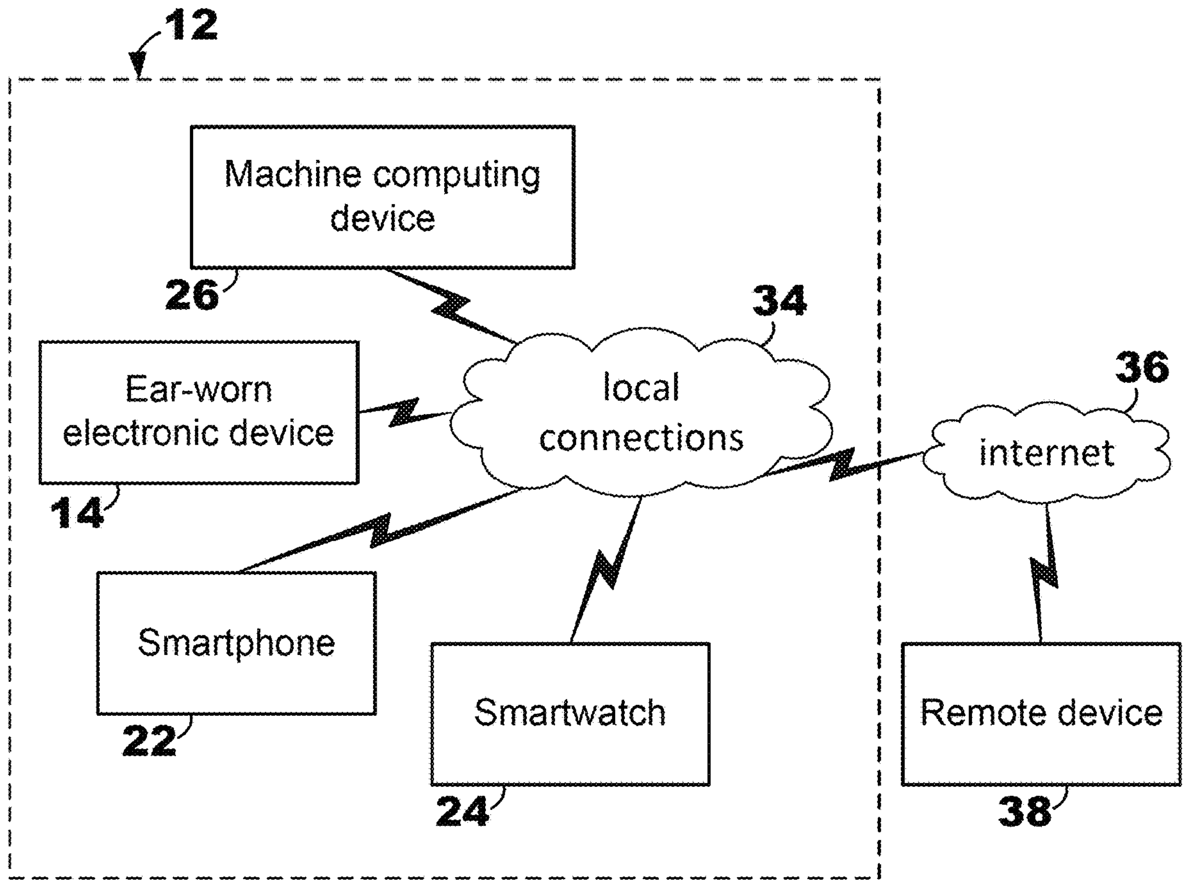
FIG. 2 is a schematic diagram showing examples of operable connections among components of the system of FIG. 1.

FIG. 2 is a schematic diagram showing examples of operable connections among components of the non-alert detection system 12. The operable connections between components may be wired, wireless, or any combination thereof.

In some embodiments, one or more components are operably coupled using local connections 34. Some examples of local connections include local networks, such as wireless body area networks (WBANs) and automotive automation wireless networks (AAWNs). In one example, a smart watch with corresponding multi-axis accelerometers may be configured to detect hand motion and provide motion data through the local connections 34.

In some embodiments, one or more components are operably coupled using the internet 36. As illustrated, the remote device 38 may be operably coupled to one or more devices connected using local connections 34 using the internet 36.

Figure 3:
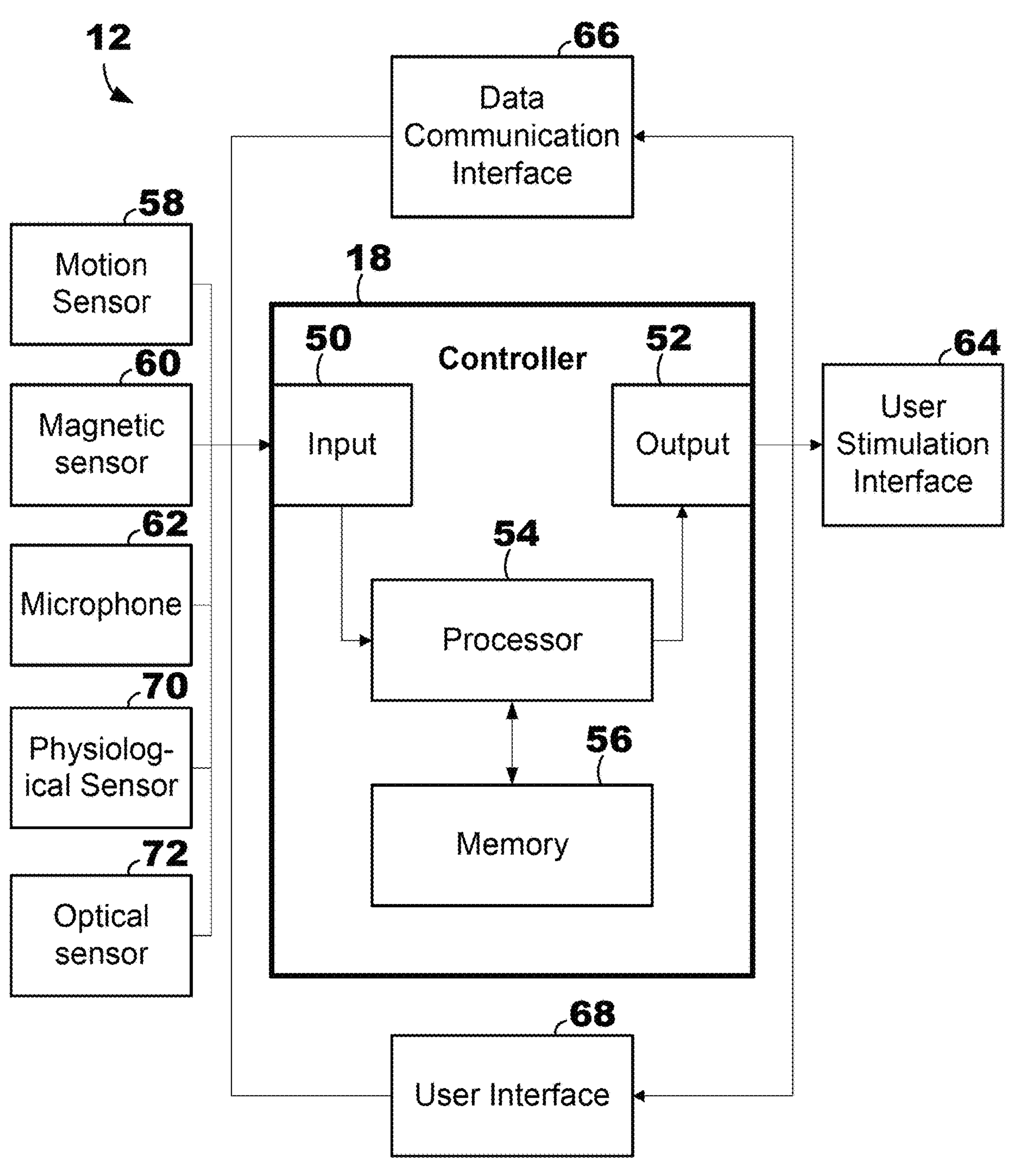
FIG. 3 is a schematic diagram of one example of a controller usable in the system of FIG. 1.
Figure 4:
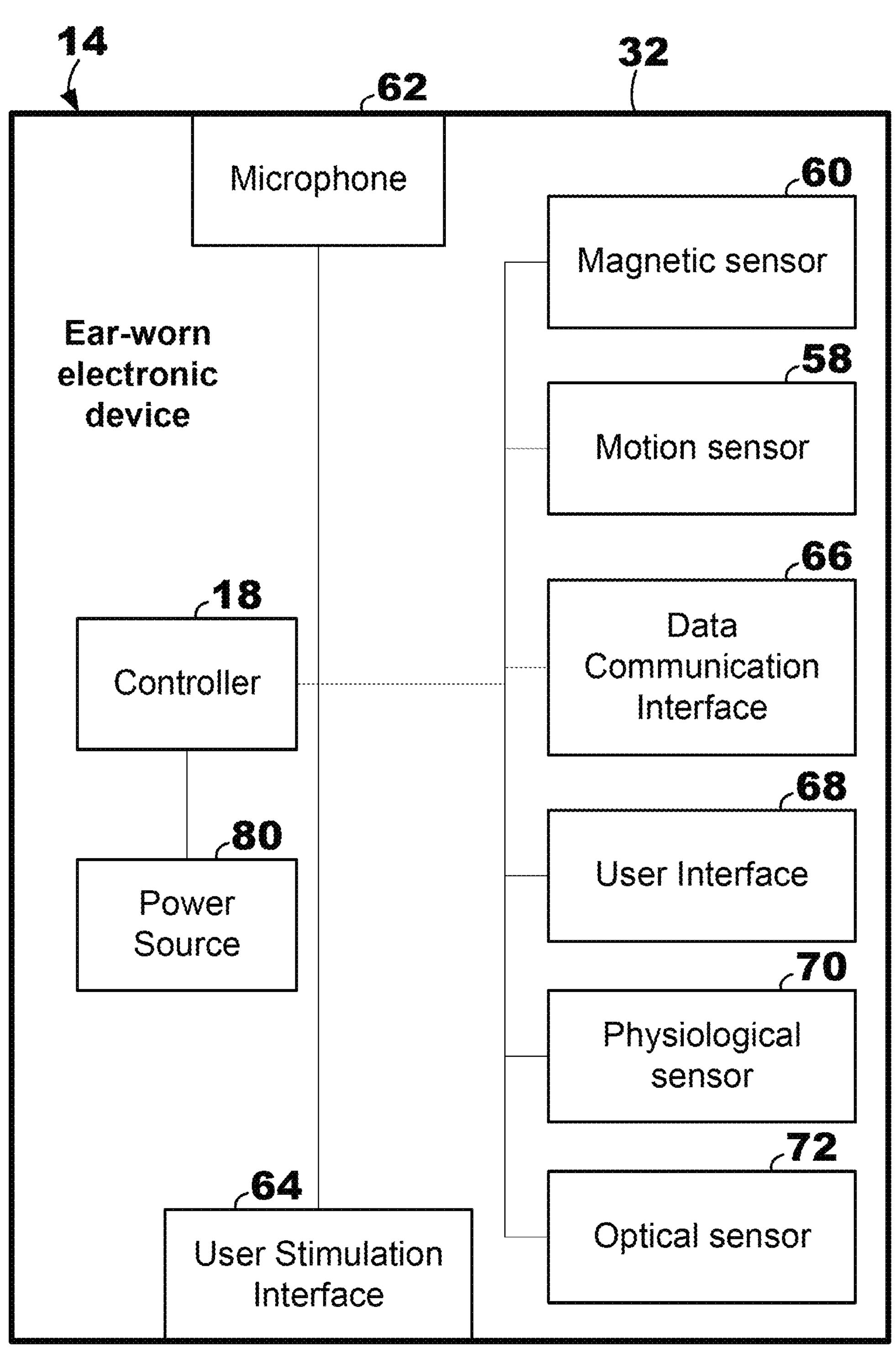
FIG. 4 is a schematic diagram showing one example of one of the ear-worn electronic devices usable in the system of FIG. 1.

FIGS. 3 and 4 show various conceptual configurations of the system 12 and the controller 18. In general, the controller 18 may be disposed in one or more components of the system 12 and operably coupled to one or more of the same or different components of the system. The controller 18 may include an input interface 50 and an output interface 52. The input interface 50 and the output interface 52 may be operably coupled to the processor 54. The processor 54 (or processing circuitry) may be operatively coupled to memory 56.

The processor 54 can be implemented as one or more of a multi-core processor, a digital signal processor (DSP), a microprocessor, a programmable controller, a general-purpose computer, a special-purpose computer, a hardware controller, a software controller, a combined hardware and software device, such as a programmable logic controller, and a programmable logic device (e.g., FPGA, ASIC). The processor 54 can include or be operatively coupled to memory 56, such as RAM, SRAM, ROM, or flash memory. In some embodiments, processing can be offloaded or shared between the processor 54 and a processor of a peripheral or accessory device.

In some embodiments, the controller 18 may be at least partially or entirely disposed in the one or more devices 14. For example, the controller 18 may be disposed in the housing 32 of one car-worn electronic device 14 or distributed among the housings of multiple devices. In some embodiments, the controller 18 may be at least partially disposed in one or more car-worn devices 14 and at least partially disposed in one or more external devices 20. For example, the controller 18 may be distributed among the housings of one or more car-worn devices 14 and one or more external devices 20. In some embodiments, the controller 18 may be at least partially or entirely disposed in one or more external devices 20. For example, the controller 18 may be disposed in the housing of at least one external device 20 or distributed among the housings of multiple external devices 20.

FIG. 3 is a schematic diagram of one example of the controller 18 operably coupled to one or more components of the system 12. FIG. 4 is a schematic diagram showing one example of one of the car-worn electronic devices 14 that may be used in the system 12, wherein the controller 18 is at least partially or entirely disposed in a housing 32 of the car-worn electronic device 14. Various other components of the system 12 may also be at least partially or entirely disposed in the housings of one or more devices 14, at least partially or entirely disposed in the housings of one or more external devices 20, or any combination of these.

The controller 18 is operably coupled to one or more of the other components of the system 12, for example, to provide and receive data. In some embodiments, the controller 18 is operably coupled to one or more of the following: a motion sensor 58, a magnetic sensor 60, a microphone 62, a user stimulation interface 64, a data communication interface 66, and a user interface 68. One or more components of the system 12 may also include a power source. The car-worn electronic device 14 may include at least one power source 80. Any suitable type of power source 80 may be used.

Other components of the system 12 may include various sensors, for example, operably coupled to the processor 54 using the input interface 50, which may be used to determine whether to initiate an alertness mode or to determine a level of alertness. The controller 18 may include or be coupled to the various one or more sensors. Non-limiting examples of sensors include: microphones (or other acoustic sensors), motion sensors (or position sensors), magnetic sensors, optical sensors, physiological sensors, and air quality sensors.

Any suitable type of motion sensor may be used, which may provide position, speed, or acceleration. Some examples of motion sensors include inertial sensors, magnetometers (such as compasses), and global positioning system (GPS) devices.

Inertial sensors may also be described as inertial measurement units (IMUs). Some examples of IMUs include accelerometers and gyroscopes. The accelerometer may be described as having one or more axes, such as a 3-axis, 6-axis, or 9-axis accelerometer. The IMU may be of a type described in U.S. Pat. No. 9,848,273 (Helwani et al.), issued Dec. 19, 2017, which is incorporated herein by reference.

Any suitable type of magnetic sensor may be used. Some examples of magnetometers include telecoils and other wireless communication antennas. A telecoil is a device including a tiny coil of wire wound around a core that induces an electric current in the coil when in the presence of a changing magnetic field. A telecoil can serve as an alternate or supplemental input device for the device 14, for example, when configured as a hearing aid. For example, a telecoil can be used as an input source instead of, or in addition to, a microphone in the device 14, allowing the device to receive a magnetic signal which represents sound. In some embodiments, a telecoil or other magnetic sensor, such as a tunnel magneto resistance (TMR) sensor, a giant magnetoresistance sensor (GMR), and the like, may be used to receive a magnetic signal representative of data either alone or in combination with a magnetic signal which represents sound.

Any suitable optical sensors may be used. Some examples of optical sensors include cameras and light level sensors (such as ambient light level sensors).

Any suitable physiological sensors may be used. Some examples of physiological sensors include neurological sensors, eye motion sensors (or eye movement sensors), temperature sensors, pressure sensors, heart rate sensors, blood pressure sensors, oxygen saturation sensors, blood glucose sensors (optical or otherwise), galvanic skin response sensors, cortisol level sensors (optical or otherwise), an electrocardiogram (ECG) sensor, myographic potential electrode sensor (EMG), blood perfusion sensors, hydrometers, perspiration sensors (or sweat sensors), and hematocrit sensors. Some physiological sensors may also be described as optical sensors or electrical signal sensors configured to detect a physiological parameter of the user 16.

Any suitable neurological sensors may be used. One example of a neurological sensor includes an electroencephalography (EEG) sensor.

Any suitable eye motion sensors may be used. Some examples of eye motion sensors include electrooculography (EOG) sensors, cameras, and pupillometry sensors.

In the illustrated embodiment, the controller 18 is operably coupled to, and may include, one or more of the following: a motion sensor 58 configured to provide motion data, a magnetic sensor 60 configured to provide magnetic data, a microphone 62 configured to provide sound data based on monitored ambient sound, a physiological sensor 70 configured to provide physiological data, an optical sensor 72 configured to provide visual data, a user stimulation interface 64 configured to provide stimulation to the user based on stimulation data (such as to the ear, head, or neck area of the user), a data communication interface 66, and a user interface 68. In some embodiments, as shown in FIG. 4, each of these other components may be disposed in one or more of the devices 14.

Motion sensors 58 (or a motion sensor arrangement) may be disposed in the ear-worn electronic device 14 and may be configured to provide motion data based on movement of the ear of the user. In general, motion sensors 58 are configured to sense motion and/or position of the user 16 when the device 14 is worn by the user. In some embodiments, motion sensors 58 may also be used to provide position data or acceleration data as motion data.

Magnetic sensors 60 may include a telecoil or telecoil arrangement having one or more (such as 1, 2, 3, or 4) telecoils. As used herein, the term "telecoil" refers to a single telecoil, magnetic sensor, multiple telecoils or magnetic sensors unless specified otherwise. A telecoil may be active (powered) telecoil or passive (only transforms received magnetic field energy). The telecoils may be positioned within the housing 32 at different angular orientations.

Any suitable type of user stimulation interface 64 may be used operably coupled to the processor 54, for example, using the output interface 52. Non-limiting examples of user stimulation interfaces 64 include transducers (for audio or sound), oscillators (for haptic vibrations), and electrical cochlear implants (for CN-VIII stimulation). In some embodiments, the user stimulation interface 64 may include a transducer in the form of a speaker or a receiver. The transducer may be capable of transmitting sound to ear drum of the user 16 when the device is worn by the user. Electrical cochlear implants are generally configured to deliver auditory stimulation, or electrical signals representative of sound to the user 16. In some embodiments, electrical cochlear implants or brainstem implants may be configured to deliver a general electrical shock to the user 16, which may serve as an alert that the user may be drowsy or otherwise non-alert.

Microphones 62 (or a microphone arrangement) may include one or more discrete microphones or a microphone arrays. A microphone array may be configured to provide microphone array beamforming. Each microphone 62 can be situated at different locations of the housing 32. As used herein, the term "microphone" refers to a single microphone or multiple microphones unless specified otherwise.

The microphones 62 may include any suitable microphone type. In some embodiments, the microphones 62 include omnidirectional microphones. In other embodiments, the microphones 62 include directional microphones. In further embodiments, the microphones 62 include a combination of one or more omnidirectional microphones and one or more directional microphones. One, some, or all of the microphones 62 may have a cardioid, hypercardioid, supercardioid or lobar pattern, for example. One, some, or all of the microphones 62 may include multi-directional microphones, such as bidirectional microphones. One, some, or all of the microphones 62 may have variable directionality, allowing for real-time selection between omnidirectional and directional patterns (for example, selecting between omni, cardioid, and shotgun patterns). In some embodiments, the polar pattern(s) of one or more microphones 62 may vary depending on the frequency range (for example, low frequencies remain in an omnidirectional pattern while high frequencies are in a directional pattern).

Depending on the device implementation, different microphone technologies may be used. For example, the device 14 may incorporate any of the following microphone technology types (or combination of types): MEMS (micro-electromechanical system) microphones (such as capacitive, piezoelectric MEMS microphones), moving coil/dynamic microphones, condenser microphones, electret microphones, ribbon microphones, crystal/ceramic microphones (such as piezoelectric microphones), boundary microphones, PZM (pressure zone microphone) microphones, and carbon microphones.

The data communication interface 66 may be operably coupled to the processor 54, for example, using the input interface 50 and the output interface 52. In general, the data communication interface 66 is configured to receive or provide data using wired or wireless techniques. In some embodiments, the data communication interface 66 includes one or more antennas for wireless communication operatively coupled to a transceiver, such as a transceiver configured for high-frequency radio (such as 2.4 GHz radio). The radio may conform to an IEEE 802.11 (such as WiFi®) or Bluetooth® (such as BLE, Bluetooth® 4. 2, 5.0, 5.1 or later) specification, for example. The device 14 may employ other radios, such as a 900 MHz radio. In addition, or alternatively, the device 14 may include a near-field magnetic induction (NFMI) sensor for effecting short-range communications (for example, for ear-to-ear communications or ear-to-kiosk communications).

The antenna may be any suitable antenna. A representative list of antennas include, but are not limited to, patch antennas, planar inverted-F antennas (PIFAs), inverted-F antennas (IFAs), chip antennas, dipoles, monopoles, dipoles with capacitive-hats, monopoles with capacitive-hats, folded dipoles or monopoles, meandered dipoles or monopoles, loop antennas, Yagi-Udi antennas, log-periodic antennas, and spiral antennas. Many of types of antenna may be implemented in the form of a flexible circuit antenna. In such embodiments, the antenna is directly integrated into a circuit flex, such that the antenna not need be soldered to a circuit that includes the transceiver or other RF components.

The user interface 68 may be operably coupled to the processor 54, for example, using the input interface 50 and the output interface 52. In some embodiments, the user interface 68 is configured to receive an input from the user 16 and to provide user input data. In some embodiments, the user interface 68 is configured to provide an alert to the user 16 and may include a display. The user input data may indicate a user command, response, or selection corresponding to the alertness mode.

User input data may be received in any suitable manner, such as using one or more of the microphone 62, the data communication interface 66, and the user interface 68. The input from the user 16 may be a touch input (or manual input), a gesture input (or visual input), or a voice input (or sound input). One example of a gesture is a hand movement captured by the optical sensor 72. One example of a touch is contact with a touchscreen or button. The user interface 68 may include one or more of the following: a tactile interface, a gesture interface, and a voice command interface. The tactile interface may include one or more manually actuatable switches (such as a push button, a toggle switch, a capacitive switch, or a resistive switch). For example, the user interface 68 may include a number of manually actuatable buttons or switches to configure various aspects of the device 14 or system 12.

In some embodiments, the user interface 68 may be at least partially or entirely disposed in a separate or external device operably coupled to the controller 18. For example, the user interface 68 may include a handheld user device 22, a separate user-worn device 24, a machine computing device 26, or even a remote electronic device 38. Various types if user input provided to those external devices may be operably communicated to the controller 18, or vice versa, for example, using the data communication interface 66.

Various functionality of the system 12 relates to determining when to enable detection of non-alert states of the user 16. In some embodiments, the system 12 may provide continuous monitoring throughout the day and may determine a risk level for fatigue, inattentiveness, or other non-alert states. In other words, the system 12 may be enabled to always detect the alertness of the user 16 when worn. In other embodiments, the system 12 may use environment and activity classification schemes to selectively enable alertness state determination, or otherwise limit the alertness state determination to when the detecting alertness would be of relevant assistance to the user 16, such as when the user is driving a vehicle or at work. Detecting non-alert states may be particularly useful when the user 16 may be operating a moving machine or vehicle. Also, preventing unnecessary indications that the user 16 that the user may be in a non-alert state may also facilitate usability and limit distractions.

In some embodiments, the system 12 may be configured to enter into and exit out of an alertness mode. In the alertness mode, the system 12 may be configured to monitor the alertness state of the user 16. Outside of the alertness mode, the system 12 may be configured to not monitor the alertness state of the user 16. One or more components of the system 12 may be configured to use the alertness mode. In some embodiments, the one or more of the devices 14 are configured to enter into an alertness mode. When the system 12 is not in the alertness mode, the system 12 may be in any other suitable mode, such as a nominal mode or hearing assistance mode, for example, when the ear-worn electronic device 14 is a hearing aid.

Various types of data, or parameters, in the sensor data may be monitored and used to determine whether to initiate the alertness mode. Such monitoring may be persistent, automatically activated, or user activated. Non-limiting examples of types of data that may be monitored include user input data, motion data, visual data, magnetic data, sound data, visual data, navigation data, and historical user data.

In some embodiments, sensor data may be used to determine whether the user 16 is in a machine operation environment. In some embodiments, detecting the car environment may include use of: acoustic sensors (sound data), inertial sensors (motion data), magnetic sensors (magnetic data), light sensors (visual data), physiological sensors (physiological data), wireless communications (data from another device or user input data), and the like.

In some embodiments, the system 12 may be configured to enter into or exit from the alertness mode in response to user input data. In some embodiments, the system 12 may be configured to detect user input to initiate (or start or activate) an alertness mode. For example, the system 12 may initiate the alertness mode based on a user logging into or unlocking operation of the system. In other embodiments, the system 12 may be configured to detect user input to not initiate an alertness mode. For example, the system 12 may determine that the alertness mode should be initiated and alert the user 16 of the impending activation. The user 16 may be provided an option to cancel initiation of the alertness mode. As described herein in more detail, the system 12 may determine to enter into the alertness mode based on other parameters. In some cases, the user 16 may be provided an option to prevent initiating of the alertness mode. In further embodiments, the system 12 may be configured to detect user input to exit from (or end) an alertness mode.

The user input data may be a user response to a query (or prompt) from the system 12. The query may be provided in any suitable manner, such as from the user stimulation interface 64, the data communication interface 66, or the user interface 68. In some embodiments, the system 12 may query the status of the user 16, for example, with "Are you driving?" as an audible or visual query. The user 16 may respond to the query using an audible or visual response, and the system 12 may enter into the alertness mode, for example, if the user responds "Yes."

In other embodiments, the system 12 may also query other aspects of the user status. For example, the system 12 may more readily enter into the alertness mode, for example, if the user responds to query that indicates a status more susceptible to experiencing a non-alert state, such as responding "Yes" to "Do you have narcolepsy?"

In further embodiments, the system 12 may provide a query paired with a system status, such as the impending activation of the alertness mode. For example, the system 12 may provide a system status and query to the user 16, such as "Alertness mode will initiate in 10 seconds. Do you want to continue initiating the alertness mode?" The user 16 may respond to the query, such as responding "No," and the system 12 may cancel entering into the alertness mode.

In some embodiments, the movement of the user 16 may be used to initiate the alertness mode. The speed of the user 16 may indicate that the user is operating a moving machine 28.

In one example, motion data may be monitored from at least one motion sensor. The speed of the user 16 may be determined based on the motion data. The alertness mode may be initiated at least partially or entirely in response to, or based on, the speed of the user. For example, the alertness mode may be initiated in response to the speed of the user crossing, or exceeding, a threshold.

Any suitable threshold of speed may be selected by one skilled in the art having the benefit of the present disclosure. In some embodiments, the threshold of speed is selected to be greater than a maximum human speed by foot, such as 10, 15, 20, 25, 30, 35, or even 40 miles per hour (mph), which may also be described equivalently in International System of Units (SI units), such as such as kilometers per hour (kph).

Any suitable technique to determine speed may be selected and used by one skilled in the art having the benefit of the present disclosure. In one example, the speed of the user 16 may be determined by integrating acceleration data in the motion data over time. In another example, the speed of the user 16 may be derived from a global positioning system (GPS) location over time.

Motion data may be provided from any suitable motion sensor disposed in one or more of the following: the car-worn electronic device 14, the handheld user device 22, the separate user-worn device 24, and the machine computing device 26.

In another example, visual data may be used to determine whether the user is in motion. Visual data may be monitored from at least one optical sensor. The acceleration, speed, or position of the user 16 may be determined based on the visual data. Whether the visual data indicates machine operation, such as movement of the vehicle, may be determined. The speed of the user 16, for example, may be determined based on the visual data. The alertness mode may be initiated at least partially or entirely in response to, or based on, the visual data. For example, the alertness mode may be initiated in response to the visual data indicating machine operation, such as the speed of the user 16 being above a threshold.

Any suitable technique to determine whether the visual data indicates machine operation may be selected and used by one skilled in the art having the benefit of the present disclosure. In one example, scene analysis of image data from a camera type of optical sensor may be used to determine whether the scene is in motion, which may indicate that the user is in motion.

Visual data may be provided from any suitable optical sensor disposed in one or more of the following: the ear-worn electronic device 14, the handheld user device 22, the separate user-worn device 24, and the machine computing device 26.

In some embodiments, whether the user 16 is in, or in the vicinity of, an operating machine may be used to initiate the alertness mode. The operation of the machine may be detected in any suitable manner.

In one example, magnetic data may be monitored from at least one magnetic sensor to initiate the alertness mode. Any suitable technique to measure and analyze magnetic data may be used known to one of ordinary skill in the art having the benefit of the present disclosure, such as techniques described in U.S. patent application Ser. No. 16/777,494, entitled "Efficient wellness measurement in ear-wearable devices," filed on Feb. 1, 2020, and U.S. Provisional Application No. 62/811,367, entitled "Hearing assistance devices with motion sickness prevention and mitigation features," filed Feb. 27, 2019, which are incorporated herein by reference.

Some machines emit a "spike" of magnetic field energy upon motor start of a vehicle or power machinery. Whether the magnetic data indicates machine operation may be determined. A "spike" in magnetic field energy that indicates machine operation, or the start of machine operation, may be determined from the magnetic data. For example, the magnetic data may be provided in the form of an electric signal corresponding to magnetic field energy. The electric signal, such as a current or voltage, or power value, may be compared to a threshold. The "spike" may be determined in response to the electric signal crossing, or exceeding, the threshold. The alertness mode may be initiated at least partially or entirely in response to, or based on, the magnetic data. For example, the alertness mode may be initiated in response to a magnetic "spike" being detected in the magnetic data.

In one example, a digital level in the magnetic sensor may activate in response to a "spike" in the magnetic field crossing the threshold, such as from the start of a car. After the car is started, the magnetic field may decrease and deactivate the digital level. In some embodiments, a "spike" in the magnetic field may also be detected in response to a hybrid or electric car under hard acceleration, which may also be used to indicate machine operation.

Any suitable technique to determine a threshold of magnetic energy to detect the magnetic "spike" may be selected and used by one skilled in the art having the benefit of the present disclosure. The threshold may be selected based on the type of machine 28, such as the particular engine starter used in the machine. In one example, a starter for a combustion engine may use a current of 250 Amps to turn over the engine, which may result in a magnetic field of 0.5 Millitesla (mT) at 1 meter. A corresponding threshold may be set at or near 0.5 mT (such as 0.3, 0.4, or 0.5 mT). In another example, other starters may generate lower magnetic fields that are a fraction of 0.5 mT, and a corresponding threshold, such as 0.1 or 0.2 mT, may be used. Thresholds for electric cars, or hybrid cars, may exceed one or more of these thresholds during hard acceleration, and a corresponding threshold to additionally, or alternatively, capture "spikes" from such hard accelerations. This is all assuming no magnetic shielding of the cabin which is an approximation. Any use of magnetic shielding in the machine 28 may also affect determination of the magnetic threshold. In some embodiments, the magnetic threshold may be calibrated for each machine 28, for example, as a factory setting or by the user 16.

Magnetic data may be provided from any suitable magnetic sensor disposed in one or more of the following: the ear-worn electronic device 14, the handheld user device 22, the separate user-worn device 24, and the machine computing device 26.

In another example, sound data may be monitored from at least one microphone to initiate the alertness mode. Some machines produce noise, or a characteristic sound, when the machine starts or is in operation. Whether the sound data indicates machine operation may be determined. The start of a combustion engine in a vehicle is one such characteristic sound that may be detected. Wind noise or road noise are other such characteristic sounds when a vehicle is in motion. The alertness mode may be initiated at least partially or entirely in response to, or based on, the sound data. For example, the alertness mode may be initiated in response to sound data indicating a motor start, wind noise, or road noise.

Sound data may be provided from any suitable microphone disposed in one or more of the following: the ear-worn electronic device 14, the handheld user device 22, the separate user-worn device 24, and the machine computing device 26.

In yet another example, an ambient light level may be determined and used to initiate the alertness mode. The ambient light level may be part of visual data. The ambient light level may indicate whether the user 16 is more susceptible to being non-alert, such as a low ambient light level at night. The alertness mode may be initiated at least partially or entirely in response to, or based on, the ambient light level. For example, the alertness mode may be initiated in response to the ambient light level being below a threshold.

Any suitable technique to determine the ambient light level may be selected and used by one skilled in the art having the benefit of the present disclosure. In one example, an optical sensor may be used to directly measure the ambient light level.

Ambient light level may be provided from any suitable optical sensor disposed in one or more of the following: the ear-worn electronic device 14, the handheld user device 22, the separate user-worn device 24, and the machine computing device 26.

In some embodiments, navigation data may be used to determine whether to initiate the alertness mode. The navigation data may indicate a navigation path of the user 16. A determination of whether the navigation path includes one or more segments that are susceptible to non-alert states may be used to determine whether to initiate the alertness mode. The alertness mode may be initiated at least partially or entirely in response to, or based on, the navigation path. For example, the navigation path may indicate that the user 16 is currently or is going to traverse a particularly straight and long segment of the navigation path and may be more susceptible to non-alert states.

Any suitable technique to determine the navigation path of the user 16 may be used known by one skilled in the art having the benefit of the present disclosure. The navigation data may be stored and provided by one or more of the following: the ear-worn electronic device 14, the handheld user device 22, the separate user-worn device 24, and the machine computing device 26. In one example, the navigation data including the navigation path of the user 16 may be provided by the handheld user device 22, such as a smartphone, or in the machine computing device 26, such as a navigation device of the vehicle.

In some embodiments, a determination of whether the user 16 is a machine operator (such as a driver) or not an operator (such as a passenger) may be used to initiate the alertness mode. The alertness mode may be initiated at least partially or entirely in response to, or based on, the operator or passenger determination. For example, the alertness mode may be initiated in response to determining that the user 16 is the operator of the machine. The operator or passenger determination may be used in conjunction, or in combination, with other determinations described herein, such as whether the user is moving above a threshold speed, to initiate the alertness mode. Various techniques to determine whether the user 16 is the operator or passenger of the machine may be selected and used by one skilled in the art having the benefit of the present disclosure.

In some embodiments, sound data may be used to determine whether the user 16 is a machine operator or passenger. In one example, a determination of whether a voice of a person different than the user 16 is in the sound data may be used to determine whether the user 16 is a machine operator or passenger. A determination that the user 16 is the operator may be made, for example, in response to determining that there are no voices (indicative of no conversation in the machine) or no voices other than the user 16. No conversations may indicate a likelihood that the user 16 is alone and by default the driver (such as in response to determining that the user 16 is in a moving vehicle of operating machine, for example, using motion data).

Additionally, or alternatively, in another example, a determination of a direction of another voice may be used to determine whether the user 16 is a machine operator or passenger. Sound data may include stereo data, or binaural data, indicative of a left channel and a right channel. Sensor signals from the right and left devices 14 may be compared to make determinations of the user's location in a car. A determination that the user 16 is the operator may be made, for example, in response to determining that there is another voice coming in the direction of a passenger seat. The direction of the passenger seat from the driver seat, for example, in a vehicle may depend on the jurisdiction. For example, in the United States, another voice in a direction to the right of driver seat indicates that the other voice may be in the passenger seat. On the other hand, speech coming from the front or left of the user may indicate the user is a passenger in the United States.

Any suitable arrangement to provide stereo data may be selected and used by one skilled in the art having the benefit of the present disclosure. In some embodiments, two devices 14 each including a microphone disposed on the left and right ears of the user 16 may be used to provide the stereo data. In general, stereo data may be provided from any suitable microphone disposed in one or more of the following: the ear-worn electronic device 14, the handheld user device 22, the separate user-worn device 24, and the machine computing device 26.

In some embodiments, motion data may be used to determine whether the user 16 is a machine operator or passenger. The motion of different body parts of the user 16 may indicate whether the user is the operator or passenger. In one example, motion data indicative of steering wheel operation may be used to determine whether the user 16 is a machine operator or passenger. The motion data from the separate user-worn device 24, such as a smartwatch, may indicate movements corresponding to operating a steering wheel, for example, to turn the vehicle. Even when a vehicle is driving in a straight line, the user 16 may make subtle adjustments to the steering, which may be detected by at least one motion sensor along the arm of the user, for example, using the smartwatch on the wrist of the user.

In another example, the motion data from the separate user-worn device 24 indicative of arm movements may be compared to motion data from the ear-worn device 14 indicative of head movements of the user 16 to determine whether the user is an operator or passenger. A determination of whether the hand movements correspond to the head movements may indicate that the user 16 is an operator, for example, who looks where the vehicle is turning.

Different tiers of sensory input from sensors coupled by WBAN may be used for determining if the user 16 wearing the device 14 is the driver or a passenger in a motor vehicle. In one example, a combination of head motion and orientation changes or absolute orientation (for example, determined using IMU motion data of the device 14) compared to a registered reference position may be used and correlated with turn signals and steering wheel motion (for example, determined using motion data of the separate user-worn device 24) to fairly accurately determine whether the user 16 is the driver.

In another example, motion data may include position data. High accuracy Bluetooth® location services may be used to locate the user 16 in the vehicle and help to determine if the user is the driver or a passenger.

In some embodiments, visual data may be used to determine whether the user 16 is a machine operator or passenger. Any suitable technique to determine whether the visual data the user 16 is an operator or passenger may be selected and used by one skilled in the art having the benefit of the present disclosure. In one example, scene analysis of image data from a camera type of optical sensor may be used to determine whether another person is seated in the passenger seat or where the steering wheel is relative to the user 16.

Visual data that includes ambient light level may also be used to determine whether the user 16 is an operator or passenger. In some embodiments, optical sensors on the right and left devices 14 may be able to detect which side of the user 16 is facing out a window versus inside a vehicle. Such determinations may also be informed by the time of day, location, calendar or moon phases, and the like.

In some embodiments, user input data may be used to determine whether the user 16 is a machine operator or passenger. The user input data may indicate a user command, response, or selection corresponding to whether the user 16 is a driver or passenger. The user input data may also be a user response to a query (or prompt) from the system 12. In one example, the user 16 may be presented with a query audibly or visually with "Are you the driver?" A determination that the user 16 is the driver may be made in response to the user vocally or manually answering "Yes."

In some embodiments, historical user data may be used to determine whether to initiate the alertness mode. A model provided with the historical user data may provide a more accurate determination of whether to initiate the alertness mode and reduce false positive initiations of the alertness mode. In one example, the historical user data may be used to train a model for determining whether to initiate the alertness mode. Non-limiting examples of historical user data include: past user input data in response to initiations of the alertness mode, user sleep cycle data, current duration the device has been worn or used, circadian rhythm data (derivable from temperature measurements), activity load of the day based on activity classification. One or more parameters or thresholds of the model for determining whether to initiate the alertness mode may be modified based on the historical user data.

Various functionality of the system 12 relates to determining whether the alertness state of the user 16 is a non-alert state. In some embodiments, the system 12 may utilize various types of data to determine the alertness state of the user 16. The alertness state may be determined, for example, in the alertness mode. Non-limiting examples of data that may be used to determine the alertness state include: user input data, motion data, sound data, data indicative of reaction speed of the user, physiological data, emotional state data, driving data, chemical sensor data, support animal data, a calculated driver error score, and historical user data.

In some embodiments, user input data may be used to determine the alertness state of the user 16. The alertness state of the user 16 may be determined at least partially or entirely based on the user input data. In some embodiments, the system 12 may query the user 16 by asking if they are awake, and the system may then wait for a user response. The user 16 may respond in various ways including: verbally, gesturally, or through manual user inputs (such as buttons on the car-worn electronic device 14 or operatively connected external devices 20). If the user 16 does not respond, or does respond but beyond a threshold duration (a slow reaction speed), the system 12 may determine a non-alert state. If the user 16 does respond, the system 12 may determine that the user is alert.

In some embodiments, motion data may be used to determine the alertness state of the user 16. In general, the movement or position of the user's head may be used to indicate whether the user 16 is in a non-alert state. The alertness state of the user 16 may be determined at least partially or entirely based on the motion data. In one example, motion data may be provided by at least one motion sensor indicating the head position of the user 16. In another example, motion data may be provided by at least one motion senor indicating head movements of the user 16.

Any suitable technique for determining the head position or head movement of the user 16 based on motion data may be selected and used by one skilled in the art having the benefit of this disclosure. In one example, at least one motion sensor in one or more ear-worn electronic devices 14 may be used to provide motion data. An inertial measurement unit (IMU), such as an accelerometer, may be used to provide motion data indicative of acceleration of the user's head. The motion data indicating acceleration may be integrated over time to provide a head speed. The head speed may be integrated over time to determine a head position.

In yet another example, motion data may be provided by at least one motion sensor indicating arm movements of the user 16. Any suitable technique for determining the arm movements of the user 16 may be selected and used by one skilled in the art having the benefit of this disclosure. The motion sensor indicating arm movements may be at least partially or entirely disposed in an external device 20, such as a smart watch.

For a user 16 driving a vehicle, even while driving on a straight, flat highway may require periodic back and forth corrections, or adjustments, of the steering wheel. While these corrective movements may differ from driver to driver, the nature of these movements may be needed to remain on the road. Significant changes in these movements may be detectable in the motion data from the smart watch. Cessation of these motions may imply a lack of active driving by the user 16. An alert or activation of an autonomous assistance system may be used in response to detecting, for example, a lack of corrective movements.

In some embodiments, motion data may be used to indicate consumption of food or beverages by the user 16. Consuming food or beverages (such as caffeinated or energy drinks) may be detected by the motion of the user 16. Any suitable technique to determine whether the user 16 is consuming food or beverages may be used, such as techniques described in U.S. Provisional Application No. 62/810,684, entitled "System and method for managing pharmacological therapeutics including a health monitoring device," filed Feb. 26, 2019, which is incorporated by reference.

In some embodiments, sound data may be used to determine the alertness state of the user 16. In general, various sounds may indicate situations when the user 16 is in a non-alert state. The alertness state of the user 16 may be determined at least partially or entirely based on the sound data. In one example, sound data may be provided by at least one microphone indicating non-alert types of sounds. Non-limiting examples of non-alert types of sounds include: a yawn or yawning speech from the user, a low speech frequency or intensity of the user (such as slow conversation or a lack of conversation), malformed speech sounds or slurred speech of the user, a rumble strip sound (indicating the user's vehicle may be drifting out of a driving lane), loud music being played (indicating the user's attempt to stay awake), sounds of other cars honking (indicating possible errant driving by the user), and eating or drinking noises (indicating the consumption of food or beverages, such as caffeine, energy, or other similar drinks by the user).

Any suitable technique for determining the sound data indicating the alertness state of the user may be selected and used by one skilled in the art having the benefit of this disclosure. The sound data may be provided from any suitable microphone disposed in one or more of the following: the ear-worn electronic device 14, the handheld user device 22, the separate user-worn device 24, and the machine computing device 26.

In another example, sound data may be provided by at least one microphone indicating a reaction speed of the user 16. The reaction speed of the user 16 may be determined at least partially or entirely based the sound data. Non-limiting examples of determining a reaction speed of the user may include one or more of the following: asking an audible question and timing an audible response of the user's input or detecting the sound of the vehicle starting to drive over a rumble strip and timing until the rumble strip sound stops.

Other types of data may also be used to indicate the reaction speed of the user 16. Non-limiting examples of data that may be used to determine the reaction speed of the user include one or more of the following: sound data, motion data (to detect head or arm movement), visual data (to detect eye movement), and physiological electrical signals (such as EEG or EOG data). Any suitable technique for determining the reaction speed of the user may be selected and used by one skilled in the art having the benefit of this disclosure. Other examples of techniques for determining the reaction speed of the user are described, for example, in U.S. Provisional Application No. 62/876,458, entitled "Ear-worn device based measurement of reaction or reflex speed," filed Jul. 29, 2019, which is incorporated by reference. Such techniques may be used to determine other indications of reaction speed, such as detecting the duration of the user's driving maneuvers, such as a lane change (for example, using motion data).

In some embodiments, physiological data may be used to determine the alertness state of the user 16. In general, various types of physiological data may indicate situations when the user 16 is in a non-alert state. The alertness state of the user 16 may be determined at least partially or entirely based on the physiological data.

In some embodiments, physiological data may include data indicating a respiration rate of the user. The respiration rate of the user may be indicated, for example, by heart rate data. Heart rate data may be used to determine a heart rate or a change in the heart rate of the user 16. In one example, the user 16 may be determined to be in non-alert state in response to detecting a low respiration rate based on a low heart rate below a threshold. In another example, the user 16 may be determined to be in a non-alert state in response to detecting a change from a low respiration rate to a higher respiration rate based on a change from a low heart rate to a higher heart rate, above a change threshold, which may indicate the user 16 has consumed caffeine or energy drinks.

In another example, physiological data may include data indicating surprise of the user 16. The surprise of the user may be indicated, for example, by heart rate data. Heart rate data may be used to determine a heart rate variability of the user 16. In one example, a high heart rate variability above a threshold may correspond with a sharp movement for lane correction, which may indicate that the user 16 is in a non-alert state.

In yet another example, physiological data may include data indicating a temperature of the user 16. The temperature may be a body temperature or a distal temperature. The temperature of the user may be indicated, for example, by temperature data. In one example, a temperature of the user 16 may be compared to a baseline conscious temperature of the user. A difference, such as plus or minus 0.5, 1, 1.5, or 2 degrees Celsius (° C.) from the baseline conscious temperature, may indicate that the user 16 is in a non-alert state.

In still a further example, physiological data may include data indicating physiological electrical signals of the user 16. The physiological electrical signals may be indicated, for example, by electrical signal data. In one example, the electrical signal data may be used to determine EEG or EOG signals from the user 16. In general, the electrical signal data may be used to determine the eye gaze data of the user 16. The electrical signal data may indicate that the user 16 is experiencing periodic alternating nystagmus eye movements, which may indicate that the user 16 is in a non-alert state.

In some embodiments, physiological data may motion data indicating head motion or position of the user 16. In one example, motion data measured by at least one motion sensor at least partially or entirely disposed on the ear-worn electronic device 14 may be used to provide data indicating head motion of the user 16. The head motion of the user 16 may be used, for example, in combination with the physiological electrical signals of the user 16 to more robustly detect nystagmus. In some embodiments, data from EOG sensors and head motion or positional sensors can be utilized to detect peripheral vestibular asymmetry (which can cause nystagmus and feelings of imbalance or dizziness to occur). Non-limiting examples of techniques for determining nystagmus using physiological electrical signals and head motion sensors are described in U.S. patent application Ser. No. 15/858,630, entitled "Fall prediction system and method of using same," filed on Feb. 13, 2017, which is incorporated by reference.

Any suitable technique for determining the physiological data indicating the alertness state of the user may be selected and used by one skilled in the art having the benefit of this disclosure. The physiological data may be provided from any suitable physiological sensor 70 disposed in one or more of the following: the ear-worn electronic device 14, the handheld user device 22, the separate user-worn device 24, and the machine computing device 26. In one example, at least one physiological sensor 70 is disposed at least partially or entirely in the ear-worn electronic device 14.

Other types of data may also be used to indicate nystagmus of the user 16. A non-limiting example of data that may be used to determine the nystagmus of the user 16 includes visual data from at least one optical sensor. In one example, the optical sensor may be at least partially or entirely disposed on an external device 20, configured to provide visual data including eye gaze data of the user. In some embodiments, at least one optical sensor may be part of or operably coupled to the machine computing device 26.

In some embodiments, emotional state data may be used to determine the alertness state of the user 16. In general, the emotional state of the user 16 may indicate when the user may be in a non-alert state. Non-limiting examples of emotional states that may indicate when the user 16 is in a non-alert state include one or more of the following: depression, sadness, distress, anger, fear, and sedation. The alertness state of the user 16 may be determined at least partially or entirely based on the emotional state data. Non-limiting examples of data that may be used to determine the emotional state of the user 16 include one or more of the following: sound data, motion data, visual data, and physiological data. Any suitable technique for determining the emotional state the user may be selected and used by one skilled in the art having the benefit of this disclosure. Examples of techniques for determining the reaction speed of the user are described, for example, in U.S. Provisional Application No. 62/800,227, entitled "Efficient wellness measurement in ear-wearable devices," filed Feb. 1, 2019, which is incorporated by reference.

In some embodiments, driving data may be used to determine the alertness state of the user 16. In general, driving data indicates the driving behavior of the user 16, which may be used to indicate when the user may be in a non-alert state. The alertness state of the user 16 may be determined at least partially or entirely based on the driving data.

In one example, a user operation adherence level based on the driving data may be used to determine the alertness state of the user 16. Measured driving data may be compared to nominal driving data. Measured driving data indicating the position, movement, or acceleration of the vehicle may be determined based on one or more of the following: motion data and visual data. The measured driving data may be provided external sensor data from an external device 20, such as motion data or visual data from the machine computing device 26. Nominal driving data may be determined based on navigation data. Navigation data may be provided, for example, from the car-worn electronic device 14, the handheld user device 22, the separate user-worn device 24, or the machine computing device 26. In some embodiments, the navigation data may indicate a predetermined navigation path of the vehicle, use of the vehicle "blinker" (or turn signal) when changing lanes or turning, or not stopping at an intersection where navigation data indicates a stop sign along the navigation path. The user operation adherence level may indicate the similarity between the measured driving data and the navigation data. In some embodiments, a user operation adherence level below a threshold may indicate a non-alert state.

In some embodiments, adherence to navigation system guidance or decision making when driving may be used to determine the alertness state. For example, if the user 16 misses several consecutive turns along their route, this may be an indication that the user is not alert. Thresholds for this determination may be made based upon a dynamic threshold based on historical user data to establish a long-term assessment of the user 16.

In some additional embodiments, driving data may indicate the interaction of the user 16 with the steering wheel, brake pedal, and accelerator pedal. Particular patterns of usage of these components of the machine 28 may indicate the user is non-alert. Such information may also be paired with motion data from other devices of the system 12.

In some embodiments, chemical sensor data may be used to determine the alertness state of the user 16. In general, chemical sensor data may indicate a condition of the user 16, which may be used to indicate when the user may be in a non-alert state. The alertness state of the user 16 may be determined at least partially or entirely based on the chemical sensor data. In one example, an impairment level based on the chemical sensor data may be used to determine the alertness state of the user 16. Any suitable technique for determining the impairment level may be selected and used by one skilled in the art having the benefit of the present disclosure. In some embodiments, the impairment level (or sobriety level) may be determined based on a blood alcohol level of the user 16. The chemical sensor data may be provided by an external device 20, such as a breathalyzer or blood monitor. In some embodiments, an impairment level above a threshold may indicate a non-alert state.

In some embodiments, support animal data indicating the reaction of a support animal may be used to determine the alertness state of the user 16. In general, support animals may be trained to detect prodromes of the user 16, such as narcolepsy, and may provide feedback detectable by the user 16 and the system 12. The alertness state of the user 16 may be determined at least partially or entirely based on the support animal data. In one example, the vocalization or movements of the support animal may be detected, such as the bark of a dog.

In some embodiments, a driver error score may be used to determine the alertness state of the user 16. In general, the driver error score may be determined based on various sensor data and used to provide an overall score indicating the alertness state of the user 16. In one example, a driver error score may be determined based on a current driver score compared to a predetermined baseline driver score. The current driver score may be determined based on measured sensor data. The predetermined baseline driver score may be determined based on previously measured sensor data or a nominal driver score. A driver error score crossing, or exceeding, a threshold may indicate a non-alert state.

The driver error score could be generated by the machine computing device 26 of a vehicle, which may be configured to provide anti-collision, safety, and automated driving mode features and services. The driver error score may be determined based on differences between the user's manual driving performance compared to what the autonomous driving mode would do. Any suitable artificial intelligence (AI) or machine learning (ML) techniques may be used to learn nominal driving behavior for the user, for example, under in an alert or non-drowsy state. The nominal driving behavior may be used as a baseline modifier for interpreting the driver error score. The AI or ML techniques may be used to discern significant sensory input from the high variability in skill and execution style of driving among different users. In response to the driver error score crossing a particular threshold, the autonomous driving mode of the machine 28 may be provided with an alert indicating a concern exists and transition to a hyper-vigilant mode. For example, the machine 28 may transition from a manual driving mode to an automated driving mode. The automated driving mode may, in some cases, be used to safely pull the vehicle to the shoulder of the road and park with hazard lights on. Alternately, or additionally, in response to being provided with the alert, the machine 28 may provide an appropriate auditory alert to stimulate the user 16 to a higher level of alertness or awareness. The user 16 may also be notified of the autonomous driving mode change.

In some embodiments, the system 12 may utilize ML techniques to adapt behaviors of the system for the specific user 16. For example, the system 12 may provide one or more corrective actions, and the system may learn which corrective actions (or combinations thereof) are most effective for the 16 user or other contexts. ML techniques may also be used to improve the accuracy of the fatigue and alertness state calculations.

In general, to mitigate false detections of drowsy driving, using many sensor data from many devices, which may be wireless coupled using a WBAN, along with an AI technique may be used to facilitate maximum detection and minimum false positives. The AI technique may incorporate one or more of the techniques described herein, including detecting whether the user 16 is an operator (or driver) or a passenger.

The AI technique may also incorporate classification of the user environment relative to the machine 28. In some embodiments, the car-worn electronic devices 14 may be used to classify vehicle environments. For example, when the head of the user 16 turns toward a backseat area of the vehicle and talks with passengers in the rear seats of the car, which may be detected using motion data and sound data from the car-worn electronic device 14, the AI technique may determine that additional, or minor, swerving of the vehicle may be expected and acceptable.

In some embodiments, the AI technique may also incorporate historical user data to facilitate prediction of the likelihood of non-alert operation by the user 16. In some embodiments, user historical data, such as the time of day, sleep cycle history and amount of time the person has gone without sleep, and physical activity level during the waking period, may be used the by AI technique to determine the likelihood of non-alert operation compared to other possible situations that may lead to a false positive.

In some embodiments, other sensor data indicative of alertness efforts by the user 16 may be used to facilitate prediction of the likelihood of non-alert operation by the user 16. In some embodiments, sound data indicating playing loud music may indicate that the user is drowsy and is playing loud music to raise driving alertness. In some embodiments, physiological data or sound data indicating the consumption of coffee, caffeine, or other energy drinks may indicate that the user is drowsy and is consuming such drinks to raise alertness. For example, physiological data, such as heartrate increases, or sound data, such as drinking sounds or verbal "logging" of beverage consumption by the user 16, may be used to detect such efforts.

In some embodiments, historical user data may be used to determine the alertness state of the user 16. A model provided with the historical user data may provide a more accurate determination of the alertness state and reduce false positive indications of a non-alert state. In one example, the historical user data may be used to train a model for determining the user 16 is in a non-alert state. Non-limiting examples of historical user data include: past user input data in response to non-alert state determinations, user sleep cycle data, current duration the device has been worn or used, circadian rhythm data (derivable from temperature measurements), activity load of the day based on activity classification. One or more parameters or thresholds of the model for determining the alertness state of the user 16 may be modified based on the historical user data.

In some embodiments, historical user data may be used to determine whether the user 16 is in a non-alert state, such as whether the user received less sleep than typical, woke up at a different time, exerted a lot of physical effort throughout the day, is expressing emotional distress, and so on. Deriving a risk level, or alertness state, related to the user's predisposition to be inattentive when driving, may also be used to adapt a threshold for making corrective actions. For example, if the system 12 determines that the user 16 may be very tired, then the system may be more aggressive at indicating the user is non-alert and providing waking alerts. If the system 12 determines that the user 16 may be energetic, the system may react more slowly to behaviors that might suggest that the user is nodding off before indicating that the user is non-alert. Further, if the system 12 knows that the user 16 has a medical condition, such as narcolepsy, then the threshold may be adapted for more aggressive alerts than a user who has typical wakefulness without narcolepsy. In other words, the threshold for determining that the user 16 is non-alert may be modified or adjusted based on the user historical data.

In some embodiments, historical user data may be used to determine whether the user 16 is likely to enter into a non-alert state. Various sensor data may be used to indicate, based on historical patterns, that the user 16 is likely to become non-alert. The system 12 may take actions in response to a determination that the user 16 is likely to enter into the non-alert state.

Various functionality of the system 12 relates to providing alert data in response to determining that the user 16 is in a non-alert state. In some embodiments, the system 12 may provide the alert data in the form of a human-perceptible alert or to a component of the system to take automatic action.

In some embodiments, a limited operation mode of the machine 28 being operated by the user 16 may be activated in response to the alert data. In one example, the alert data may be provided to the machine computing device 26 of the machine 28. The machine 28 may enter into a limited operation mode in response to receive the alert data indicating that the user 16 is in a non-alert state. The machine computing device 26 of a vehicle may initiate an autonomous or semi-autonomous driving mode. The machine computing device 26 of a stationary machine may operate a shutdown or other limited operation mode.

In some embodiments, the system 12 may scan for wireless protocol identifiers, such as Bluetooth device advertisements, which allow the system to determine the make and model of a vehicle. In some embodiments, the system 12 may make a determination that the vehicle is manually driven, semi-autonomous, or fully autonomous. The system 12 may connect with the machine computing device 26 of the vehicle to access key metrics of telemetry, navigation system guidance, and other useful information. The system 12 may connect to the vehicle to control media players, lights, environmental control systems (such as air conditioning), and autonomous driving functions (such as parking of the vehicle).

In some embodiments, a user-perceptible alert may be provided in response to alert data. The user-perceptible alert may be configured to inform the user 16 of being in the non-alert state. The user 16 may take action in response to the user-perceptible alert to address the non-alert state. In some embodiments, the user-perceptible alert is configured to change the alertness state of the user 16 from a non-alert state to an alert state.

Any suitable user-perceptible alert may be selected and used by one skilled in the art having the benefit of the present disclosure. Non-limiting examples of user-perceptible alerts include one or more of the following: an audible alert, a haptic alert, an electrical stimulation alert, and a visual alert. The audible alert may be provided using any suitable user stimulation interface 64, which may be disposed in one or more of the following: the ear-worn electronic device 14, the handheld user device 22, the separate user-worn device 24, and the machine computing device 26. A haptic alert may be provided using any suitable haptic device in contact with or proximate to the user 16 and may be disposed in one or more of the following: the ear-worn electronic device 14, the handheld user device 22, the separate user-worn device 24, and the machine computing device 26. An electrical stimulation alert may be provided using any suitable electrical stimulation circuit of the user stimulation interface 64 in contact with the user 16 and may be disposed in, for example, the device 14. A visual alert may be provided using any suitable display, such as the display and may be disposed in one or more of the following: the handheld user device 22, the separate user-worn device 24, and the machine computing device 26.

Figure 5:
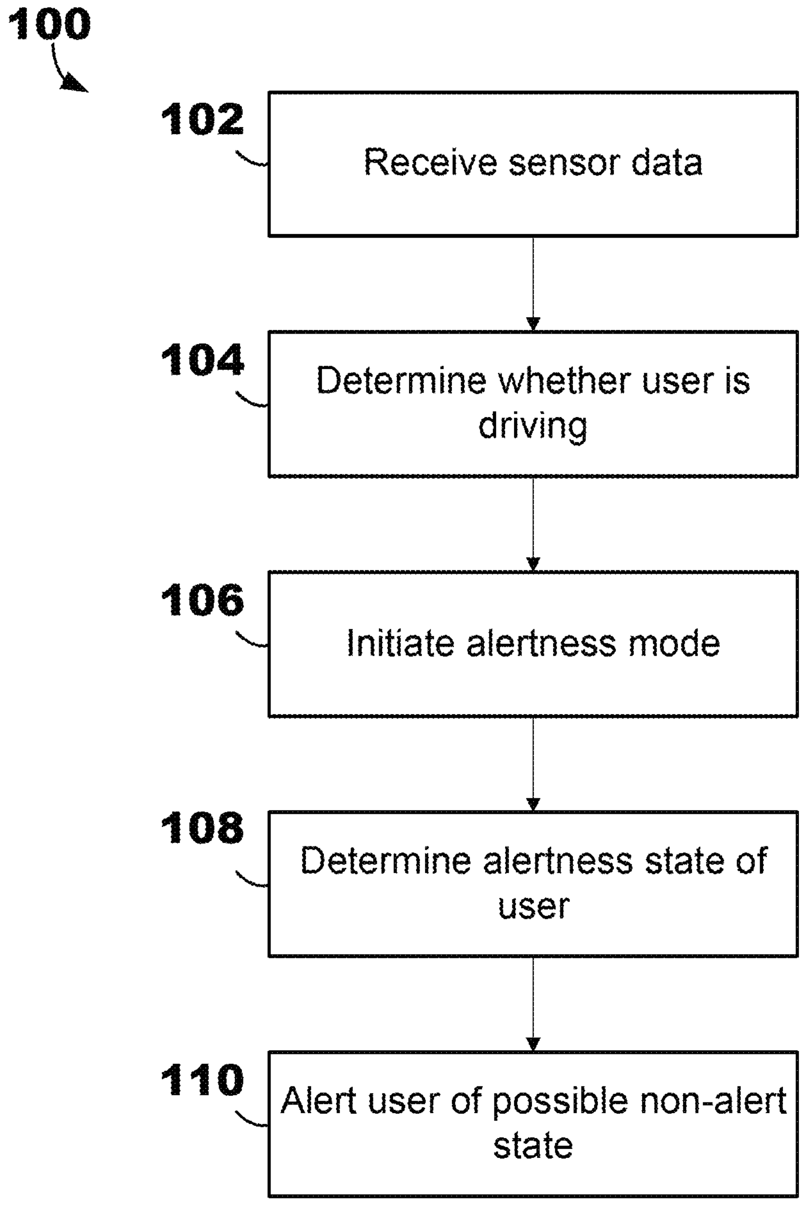
FIG. 5 is a flowchart diagram of one example of a method of detecting a non-alert state of the user usable with the system of FIG. 1.

FIG. 5 is a flowchart diagram of one example of a method 100 of detecting a non-alert state of a user, such as the user 16. The method 100 may be used to detect the non-alert state of the user who may be driving a vehicle. The method 100 may include part or all of one or more of blocks 102 to 110 described herein.

In block 102, sensor data may be received, for example, from an ear-worn electronic device, such as one or more of the ear-worn electronic devices 14, or an external device, such as one or more of the external devices 20.

In block 104, the sensor data may be used to determine whether the user is driving. In some embodiments, data from an IMU in the ear-worn electronic device may be used to determine whether the user is driving a motor vehicle. The IMU data may indicate acceleration to a speed crossing, or exceeding, a threshold. In one example, accelerometer data from the IMU may be integrated along the forward axis to determine the speed. In another example, positional data from GPS data provided by an external device such as a smart phone, smart watch, or machine computing system (such as the on-board navigation system of a vehicle) over time may be used to determine the speed.

By integrating the forward axis accelerometer measurements in time in the hearing instruments a determination can be made that the user is now driving. As an alternative, a smart phone or smart watch equipped with GPS or the car's driver assistance module can aid in the determination if the user is driving.

In block 106, an alertness mode may be initiated, or activated, in response to determining that the user is driving. The alertness mode may be activated automatically, through a user setting, or by announcing via the user stimulation interface, such as one disposed in the ear-worn electronic device, that activation of the alertness mode is imminent unless an abort command is given by the user.

Following confirmation that the driver is moving, the alertness mode may be automatically activated. The driver may be alerted to activate the drowsy detection mode using the user stimulation device of the ear-worn electronic device. The hearing instruments of ear-worn devices themselves may be able to make the determination thereafter if the driver is showing signs of drowsiness based on inputs from the IMU sensors, heartrate sensors and temperature sensors located within the hearing instruments, or the information from the sensors may be uploaded to another device such as a smart phone, smart watch, or the car's driver assistance device to make the determination and alert the driver or take corrective action in the case of the driver assistance module.

In block 108, an alertness state of the user may be determined, for example, in response to initiating the alertness mode. In some embodiments, determining the alertness state of the user may include determining the orientation of the user's nominal head position at the point of crossing a threshold speed, such as a road speed. In some embodiments, determining the alertness state of the user may include determining whether the drivers head has movements that are indicative of drowsiness or other non-alert state.

Further, in some embodiments, determining the alertness state of the user may include determining the heart rate of the user compared with a conscious baseline threshold as additional indication of drowsiness or other non-alert state. In some embodiments, determining the alertness state of the user may include determining the distal temperature of the user via a temperature sensor, or thermo sensor, which may be disposed in the ear-worn electronic device compared with a conscious baseline threshold as additional indication of drowsiness or other non-alert state.

In block 110, the user may be alerted of a possible non-alert state. The user may be alerted using audible, haptic vibrations, electrical stimulus, visual, or any combination thereof from within one or more of the ear-worn electronic devices indicating that the user may have become drowsy.

In another example, a method similar to the method 100 may be used when operating stationary machines, such as power tools or heavy equipment. In some embodiments, instead of speed, detecting sounds from the start or operation of the machine may be used to activate the alertness mode.

Thus, various embodiments of non-alert detection are disclosed. Although reference is made herein to the accompanying set of drawings that form part of this disclosure, one of at least ordinary skill in the art will appreciate that various adaptations and modifications of the embodiments described herein are within, or do not depart from, the scope of this disclosure. For example, aspects of the embodiments described herein may be combined in a variety of ways with each other. Therefore, it is to be understood that, within the scope of the appended claims, the claimed invention may be practiced other than as explicitly described herein.

All references and publications cited herein are expressly incorporated herein by reference in their entirety for all purposes, except to the extent any aspect directly contradicts this disclosure.

All scientific and technical terms used herein have meanings commonly used in the art unless otherwise specified. The definitions provided herein are to facilitate understanding of certain terms used frequently herein and are not meant to limit the scope of the present disclosure.

Unless otherwise indicated, all numbers expressing feature sizes, amounts, and physical properties used in the specification and claims may be understood as being modified either by the term "exactly" or "about." Accordingly, unless indicated to the contrary, the numerical parameters set forth in the foregoing specification and attached claims are approximations that can vary depending upon the desired properties sought to be obtained by those skilled in the art utilizing the teachings disclosed herein or, for example, within typical ranges of experimental error.

The recitation of numerical ranges by endpoints includes all numbers subsumed within that range (e.g. 1 to 5 includes 1, 1.5, 2, 2.75, 3, 3.80, 4, and 5) and any range within that range. Herein, the terms "up to" or "no greater than" a number (e.g., up to 50) includes the number (e.g., 50), and the term "no less than" a number (e.g., no less than 5) includes the number (e.g., 5).

As used herein, the term "configured to" may be used interchangeably with the terms "adapted to" or "structured to" unless the content of this disclosure clearly dictates otherwise.

The singular forms "a," "an," and "the" encompass embodiments having plural referents unless its context clearly dictates otherwise.

The phrases "at least one of," "comprises at least one of," and "one or more of" followed by a list refers to any one of the items in the list and any combination of two or more items in the list.

What is claimed is:

1. A method, comprising:
- receiving sensor data from an ear-worn electronic device disposed at least partially in the ear of a user, the sensor data comprising sound data from at least one microphone of the ear-worn electronic device;
- determining a reaction speed of the user based at least in part on the sound data;
- determining an alertness state of the user is a non-alert state based on at least determining the reaction speed does not satisfy a threshold reaction speed; and
- in response to determining the alertness state of the user is the non-alert state, providing alert data to a user stimulation interface of the ear-worn electronic device or to an external device.

2. The method according to claim 1, wherein the sensor data comprises one or both of:
- motion data indicating a head position of the user; and
- motion data indicating head movements of the user.

3. The method according to claim 1, wherein the sensor data comprises physiological data including one or more of:
- data indicating a respiration rate of the user;
- data indicating surprise of the user;
- data indicating a temperature of the user;
- data indicating physiological electrical signals of the user indicative of eye gaze; and
- data indicating head motion or position of the user.

4. The method according to claim 1, wherein the sensor data comprises one or both of:
- data indicating a reaction speed of the user; and
- emotional state data.

5. The method according to claim 1, further comprising determining the alertness state of the user further based on external sensor data.

6. The method according to claim 5, wherein the external sensor data comprises motion data from at least one motion sensor indicating arm movements of the user.

7. The method according to claim 5, wherein the external sensor data comprises visual data from at least one optical sensor comprising eye gaze data of the user.

8. The method according to claim 7, wherein the external sensor data comprises driving data, the method further comprising determining a user operation adherence level based on the driving data.

9. The method according to claim 5, wherein the external sensor data comprises chemical sensor data indicating an impairment level.

10. The method according to claim 1, further comprising receiving support animal data indicating a reaction of a support animal of the user.

11. The method according to claim 1, further comprising:
- determining a driver error score based on a current driver score to a predetermined baseline driver score; and
- determining an alertness state of the user further based on the driver error score.

12. The method according to claim 1, further comprising updating a model to determine the alertness state of the user based on historical user data to reduce false positive indications of non-alert states.

13. The method according to claim 1, further comprising providing the alert data to an external device to activate an autonomous or semi-autonomous operational mode of a machine being operated by the user.

14. The method according to claim 1, wherein a user-perceptible alert is provided in response to the alert data comprising one of more of the following: an audible alert, a haptic alert, an electrical stimulation alert, and a visual alert.

15. The method according to claim 1, wherein the sound data comprises sound produced by a vehicle operated by the user running over a rumble strip.

16. The method according to claim 1, wherein the sensor data comprises data indicative of the user's circadian rhythm, and the alertness state of the user is determined based on the circadian rhythm data.

17. The method according to claim 1, further comprising outputting an audible sound and detecting an audible response of the user, wherein the sound data includes the audible response of the user.

18. The method according to claim 1, further comprising detecting the start of a sound and determining an amount of time from the start of the sound until the sound stops, wherein determining the reaction speed is further based on the amount of time from the start of the sound until the sound stops.

19. A method, comprising:
- receiving sensor data from an ear-worn electronic device disposed at least partially in the ear of a user, the sensor data comprising sound data from at least one microphone of the ear-worn electronic device, the sensor data further comprising motion data from a motion sensor of the ear-worn electronic device;
- determining a reaction speed of the user based at least in part on the sound data and the motion data;

determining an alertness state of the user is a non-alert state based on determining the reaction speed does not satisfy a threshold reaction speed; and in response to determining the alertness state of the user is the non-alert state, providing alert data to a user stimulation interface of the ear-worn electronic device or to an external device.

20. The method according to claim 19, wherein the motion data is indicative of one or both of head position of the user and head movements of the user.

21. The method according to claim 19, wherein the sound data comprises sound produced by a vehicle operated by the user running over a rumble strip.

22. The method according to claim 19, wherein the sensor data comprises data indicative of the user's circadian rhythm, and the alertness state of the user is determined based on the circadian rhythm data.

* * * * *